(12) United States Patent
Matalon et al.

(10) Patent No.: US 8,973,574 B2
(45) Date of Patent: Mar. 10, 2015

(54) SYSTEM FOR RESPIRATORY EMERGENCIES

(75) Inventors: Dror Matalon, Meytar (IL); Ehud Kantor, Hod-HaSharon (IL)

(73) Assignee: Inovytec Medical Solutions Ltd, Nahal Oz (IL)

( * ) Notice: Subject to any disclaimer, the term of this patent is extended or adjusted under 35 U.S.C. 154(b) by 496 days.

(21) Appl. No.: 13/381,986

(22) PCT Filed: Jul. 7, 2010

(86) PCT No.: PCT/IL2010/000546
§ 371 (c)(1),
(2), (4) Date: Jan. 3, 2012

(87) PCT Pub. No.: WO2011/004371
PCT Pub. Date: Jan. 13, 2011

(65) Prior Publication Data
US 2012/0097158 A1 Apr. 26, 2012

Related U.S. Application Data

(60) Provisional application No. 61/224,072, filed on Jul. 9, 2009.

(51) Int. Cl.
*A61G 13/12* (2006.01)
*A61B 5/00* (2006.01)
*A61B 5/0205* (2006.01)
*A61B 5/087* (2006.01)
(Continued)

(52) U.S. Cl.
CPC .......... *A61G 13/1215* (2013.01); *A61B 5/0002* (2013.01); *A61B 5/0205* (2013.01); *A61B 5/021* (2013.01); *A61B 5/0816* (2013.01); *A61B 5/087* (2013.01); *A61B 5/11* (2013.01); *A61B 5/1112* (2013.01); *A61B 5/14551* (2013.01); *A61B 5/70* (2013.01); *A61B 2505/01* (2013.01); *A61G 2203/46* (2013.01)
USPC ............ 128/202.18; 128/204.18; 128/204.21; 128/204.23

(58) Field of Classification Search
CPC .... A61B 5/0002; A61B 5/0205; A61B 5/087; A61B 5/1112; A61G 13/1215; A61G 13/1265; A61G 13/121; A47C 20/02; A47C 27/08; A47G 9/1027
USPC ............. 128/200.24, 202.28, 204.18, 204.21, 128/204.23, 205.13–205.17, 205.23, 128/205.25, 845; 5/632, 644, 655.3, 633, 5/634; 607/5
See application file for complete search history.

(56) References Cited

U.S. PATENT DOCUMENTS 3,351,052 A * 11/1967 Hewson .................... 601/106
3,461,858 A * 8/1969 Michelson ................. 601/41
(Continued)

OTHER PUBLICATIONS

International Search Report mailed Oct. 25, 2010 for PCT10/00546.

*Primary Examiner* — Annette Dixon
(74) *Attorney, Agent, or Firm* — Symbus Law Group, LLC; Clifford D. Hyra

(57) ABSTRACT

A portable resuscitation system is provided. The system includes a housing for enclosing a ventilation device and a vital signs tracking device. The housing is anatomically designed for use as a neck support for opening an airway of a subject in a supine position and optionally includes mechanism for modifying the height or angle of the neck support.

17 Claims, 2 Drawing Sheets

(51) Int. Cl.
  *A61B 5/021* (2006.01)
  *A61B 5/08* (2006.01)
  *A61B 5/11* (2006.01)
  *A61B 5/1455* (2006.01)

(56) References Cited

U.S. PATENT DOCUMENTS

| | | | |
|---|---|---|---|
| 3,923,054 A * | 12/1975 | Bauer, Jr. | 128/202.18 |
| 4,196,725 A | 4/1980 | Gunderson | |
| 4,297,999 A | 11/1981 | Kitrell | |
| 5,398,676 A * | 3/1995 | Press et al. | 128/204.23 |
| 5,694,929 A * | 12/1997 | Christopher | 128/207.14 |
| 5,720,770 A * | 2/1998 | Nappholz et al. | 607/30 |
| 6,349,724 B1 * | 2/2002 | Burton et al. | 128/204.18 |
| 7,013,898 B2 * | 3/2006 | Rashad et al. | 128/207.18 |
| 7,127,758 B2 * | 10/2006 | Gabbay | 5/633 |
| 7,337,777 B1 * | 3/2008 | Islava | 128/202.28 |
| 7,383,599 B2 * | 6/2008 | Gabbay | 5/633 |
| 2006/0069326 A1 | 3/2006 | Heath | |
| 2006/0180146 A1 * | 8/2006 | Thompson et al. | 128/202.28 |
| 2007/0000494 A1 | 1/2007 | Banner et al. | |
| 2009/0044799 A1 * | 2/2009 | Qiu | 128/200.26 |

* cited by examiner

SYSTEM FOR RESPIRATORY EMERGENCIES

This application claims the benefit of U.S. Provisional Application No. 61/224,072 filed Jul. 9, 2009, which is hereby incorporated by reference in its entirety.

FIELD AND BACKGROUND OF THE INVENTION

The present invention relates to a portable respiratory assist system which can be used by non-experienced individuals to treat medical emergencies and to alert medical responder services.

Systems for treating medical emergencies are routinely used in hospital settings or ambulances. Such systems generally include an oxygen source, suction devices to clear obstructed airways, as well as crash carts which can be used for heart defibrillation.

Since such systems are dedicated for use by professional trained personnel in hospital systems' they are useless when a patient is in transit or in emergencies which cannot be treated at a hospital by professional personnel.

In order to overcome these limitations, attempts have been made to provide some form of a mobile system that can be used away from the hospital settings. Unfortunately most of these devices are very cumbersome and have failed to properly address the problem of providing an easy to use, rapidly deployable portable system for providing respiratory support. In addition, these systems typically require an operator with experience and as such cannot be used by a layperson.

The resuscitation apparatus described in U.S. Pat. No. 4,297,999 attempts to overcome some of the limitations described above by providing a resuscitation unit which guides proper resuscitation. This apparatus includes a neck support unit for enabling head tilting suitable for airway opening and a rhythm unit for indicating to an operator the correct heart message and ventilation pace.

Although the above described apparatus simplifies the resuscitation procedure, it is configured such that functional components thereof are exposed to potential damage during transport while being cumbersome to deploy and operate in emergency situations.

Therefore an object of the present invention is to provide a portable resuscitation system that is lightweight and rapidly deployable while also being configured such that the functional components of the system are protected from damage during transport and use.

SUMMARY OF THE INVENTION

According to one aspect of the present invention there is provided a portable system comprising a housing for enclosing a ventilation device and a vital signs tracking device, the housing being configured for use as a neck support for opening an airway of a subject in a supine position.

According to further features in preferred embodiments of the invention described below, the system further comprises a communications unit for transmitting data collected via the vital signs tracking device.

According to still further features in the described preferred embodiments the system further comprises a location tracking unit for determining a geographic location of the system.

According to still further features in the described preferred embodiments the system further comprises a user interface for relaying commands and/or providing data to an operator.

According to still further features in the described preferred embodiments the ventilation device includes a pressurized oxygen source and a face mask.

According to still further features in the described preferred embodiments the transmitter is an RF transmitter.

According to still further features in the described preferred embodiments the vital signs tracking device tracks a respiration rate and a heart rate.

According to still further features in the described preferred embodiments the location tracking unit is a GPS unit.

According to still further features in the described preferred embodiments the communications unit is capable of automatically transmitting vital signs to a medical facility.

According to still further features in the described preferred embodiments the communications unit is capable of receiving data from a medical facility.

According to still further features in the described preferred embodiments the housing includes a recess at a top surface thereof, the recess being designed for accommodating a neck of the subject in a manner which extends the neck to open an airway of the subject.

According to still further features in the described preferred embodiments the vital signs tracking device is a wrist cuff.

According to still further features in the described preferred embodiments the ventilation device includes a respiration sensor.

According to still further features in the described preferred embodiments the respiration sensor is positioned in a reservoir of the face mask.

According to still further features in the described preferred embodiments the respiration sensor is a pressure transducer.

According to still further features in the described preferred embodiments the respiration sensor can be used to determine a respiration parameter selected from the group consisting of inspiration/expiration ratio, respiration rate and respiratory volume.

According to still further features in the described preferred embodiments the system further comprises a mechanism for modifying a head angle of the subject when in the supine position.

According to still further features in the described preferred embodiments the mechanism is operated manually.

According to still further features in the described preferred embodiments the mechanism is operated automatically according to data from the respiration sensor.

According to still further features in the described preferred embodiments the respiration parameter is selected from the group consisting of inspiration/expiration ratio, respiration rate and respiratory volume.

The present invention successfully addresses the shortcomings of the presently known configurations by providing a portable resuscitation system which is easy to carry and deploy while being configured for protecting functional components during transport, as well as being configured for automatically alerting medical responders and enabling a layperson to provide emergency medical assistance.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
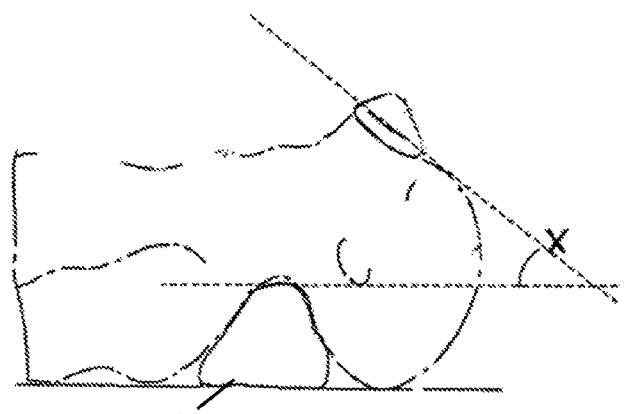
FIG. 1 illustrates the head tilting and airway opening resulting from use of the head support unit of the present invention.

The present invention is of a system which can be used for resuscitation by layperson and for automatically alerting emergency responders.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As is described in the background of the invention section above, prior attempts have failed to provide a resuscitation system which can be rapidly and easily deployed while being designed for protecting the sensitive functional components during transport and storage.

While reducing the present invention to practice, the present inventors have devised a portable resuscitation system which addresses the shortcomings of prior art systems.

The present system is designed for operation in any medical emergency situation including respiratory, cardiac or trauma emergencies. Emergency situations occur when least expected and are often a result of airway obstruction and hypoxemia and therefore airway stabilization and supplementary oxygen delivery is key to resuscitation. The present system is designed to provide basic resuscitation functionality and supplement CPR for non-breathing cardiac arrest victims.

The present system is easy to use, light weight and operable by a single layperson. The components of the system are enclosed in a single compact housing which is anatomically designed to function as neck support for tilting the head and opening the airways, so as to ensure appropriate ventilatory respirations. The present system also includes a user interface for providing vocal or visual instructions to the operator as well as provides sensors for measuring vital signs and communication functionality for alerting medical responders.

Thus, according to one aspect of the present invention there is provided a portable resuscitation system. As used herein, the term "resuscitation" refers to enhancing vital signs of a person. In that respect, resuscitation can be reviving an unconscious person, providing ventilation and oxygen as needed or supporting a person having breathing difficulties.

The present system includes a housing for enclosing a ventilation and oxygenation device and a vital signs tracking device. The housing is configured for use as a neck support for opening an airway of a subject in a supine position. Thus, the housing of the present system functions as both an easily carried 'container' for storing and protecting the components of the system and as a neck support for ensuring a correct head tilting and maintaining the airway open for ventilation.

The vital sign tracking device can be any device suitable for monitoring and tracking vital signs such as respiration, heart rate, temperature, blood pressure and pulse oxymeter saturation. Devices for performing such functions are well known to the ordinary skilled artisan.

The present system further includes a location tracking unit (e.g. GPS) for determining a geographic location of the system and thus of the treated individual. The present system further includes a communications unit (e.g. RF transceiver, Bluetooth or a cellular communications device) for transmitting data collected via said vital signs tracking device and for also transmitting the location data collected by the location tracking device. Transmission can be directed to a specific medical facility, an emergency medical response provider and the like. Transmission of vital signs can be in real time or following collection of vital signs over a predetermined time period (e.g. several minutes). In any case, the transmitted vital signs data can be interpreted by a medical professional, which can optionally communicate with the operator of the system (via the transceiver and user interface) and provide the operator with instructions as to what action to perform. Alternatively, the medical professional can directly interact with the present system (once set up and running by the operator) and modify parameters such as ventilation rate and the like.

A user interface of the present system includes audio and or visual communications means. For example, the present system can include a microphone and speaker and/or a display. The user interface can also include controls for setting various parameters of the system (e.g. ventilation rate, oxygenation level).

The ventilation and oxygenation device includes a pressurized oxygen source and a face mask and tubing all stored within the housing.

Figure 2:
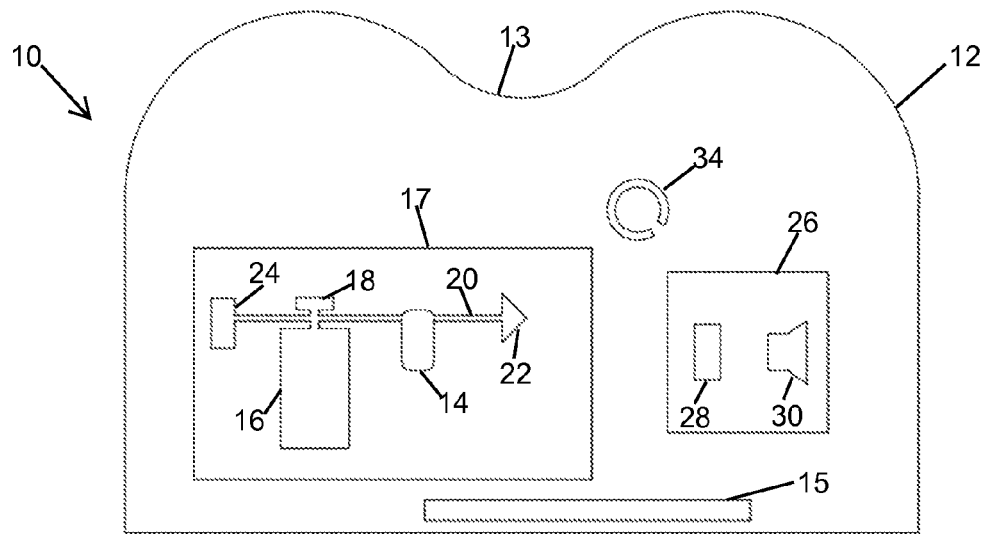
FIG. 2 illustrates the components of the present system.
Figure 3:
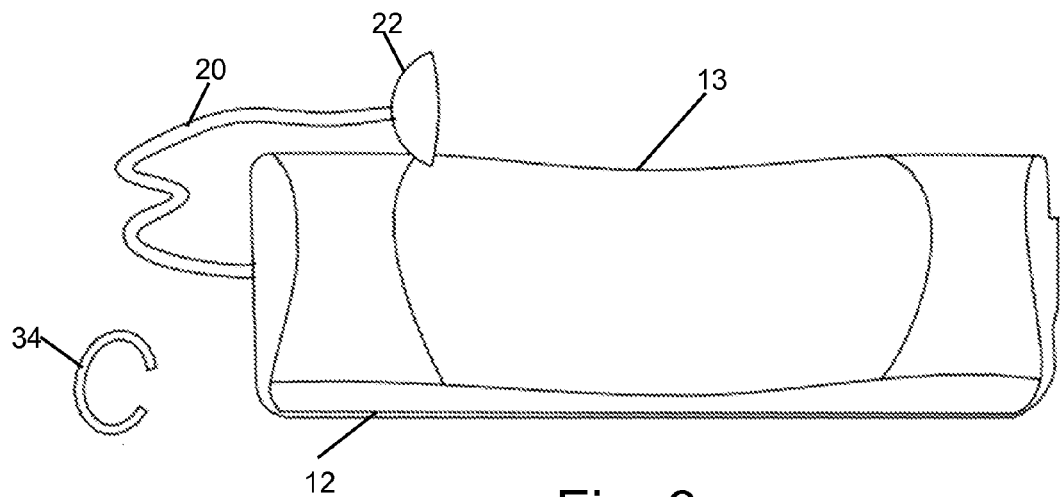
FIG. 3 illustrates one preferred configuration of the present system.

FIGS. 2-3 illustrate the various components of the present system which is referred to hereinunder as system 10. FIG. 1 illustrates housing 12 which is anatomically designed to provide neck extension (resulting in head tilt and chin lift) when placed under the neck of an individual in a supine position. Neck extension opens any obstruction caused by relaxation of the soft tissues of the oropharynx and thus ensures an open airway.

As is shown in FIG. 1, housing 12 is designed for placement below the neck in order to achieve a head tilt position with hyperextension of 42 degrees (+/−3 degrees). This angle (the art accepted angle) is measured between the longitudinal axis of the patient surface and through the longitudinal axis of the facemask positioned on the face (a line connecting the orbital ridge and the lateral corner of the mouth). To ensure correct placement, external surface of housing 12 can be printed with instructions/diagram for correct use.

Correct use of housing 12 as prescribed will prevent the head of the treated individual from assuming other unwanted positions which may not fully support an open airway or may even obstruct the airway as often happens when a pillow is placed behind the head. An open airway will facilitate spontaneous breathing and prevent any obstruction to oxygen flow.

Housing 12 can be rectangular in shape with a width of 22-38 cm. The top surface of Housing 12 includes a headrest 13 (which is preferably a semi-circular recess—see FIGS. 2 and 3) which is designed for accepting the neck of an individual and supporting it in an extended position, thereby enabling head tilting. The headrest 13 occupies 10-25 cm of the width of housing 12. To ensure optimal head tilting, the top surface of housing 12 includes markings indicating to an operator of system 10 how to correctly position housing 12 for optimal neck extension (42±3 degrees, as shown in FIG. 1).

Headrest 13 can be designed such that once housing 12 is placed under the neck of an individual, the semi-circular shape 'traps' the neck in position and prevent movement thereof.

To provide the desired head tilting angle, headrest 13 is designed for elevating the neck of the individual 6-15 cm from the floor when housing 12 is positioned under the neck of the individual. The bottom surface of housing 12 is coated with, or fabricated from, an anti-skid/slip material such as rubber in order to ensure that the head of the individual remains in the tilted position. If such movement is detected by the system or if oxygen supply is interrupted, system 10 issues a warning message.

Housing 12 can also include a mechanism for adjusting the head angle of the treated individual, such a mechanism can employ motors, servos, inflatable bladders and the like. Mechanism 15 can be operated manually or automatically to either change the shape or height of headrest 13 or change the position or angle of housing 12 and thereby modify the angulation of the treated individual.

Mechanism 15 can be operated by a user of system 10 (an operator of system 10 or the treated individual) or operated automatically in closed loop with the sensor data (as is further described in Example 1).

One preferred example of mechanism 15 includes inflatable bladders which can be inflated via blowers or compressed gas and deflated via an escape valve.

FIG. 2 schematically illustrates the preferred components enclosed in housing (12 in FIG. 1 and FIG. 3) of system 10 (FIG. 3). A ventilation device 17 typically includes an oxygen tank 16, a regulator 18, tubing 20, a face mask 22 and a reservoir 14. Tank 16 also includes a refill valve 24 for replenishing lost oxygen following use. Tank 16 is preferably a 240-450 liter tank with a length of 17-30 cm. System 10 further includes a vital signs record unit 26 which includes a processing unit for processing sensor data, an emergency cellular transceiver and GPS unit 28 and a user interface (speaker shown) 30 all co-housed in a single case with related circuitry and a power source and switch. The processing unit includes a software application designed for processing data received from sensors positioned in face mask 22 (flow sensors) and in wrist cuff 34 (pulse oxymetry, blood pressure, temperature).

Flow sensor data can include respiration rate, volume, inspiration/expiration ratio and distal blood pressure. Such data can be used by the processing unit to determine if the treated individual is in respiratory distress which may be caused by sub-optimal head angle, trauma, stroke and the like.

Wrist cuff sensor data can include vital signs such as heart rate, blood pressure, blood oxygen saturation and the like and can be used by the processing unit to determine the physiological condition of the treated individual. Data from mask 22 can be correlated with the data from wrist cuff 34 to provide, for example, an indication whether respiratory distress is a result of incorrect head angle or trauma.

Once system 10 is turned on an emergency service is alerted (via transceiver or cellular unit) and the location of the treated individual is identified by GPS unit 28 and relayed to the emergency service. Simple medical instructions are then issued through speaker 30 (FIG. 2) providing the operator with step by step instructions in placing the oxygen mask and connecting vital signs sensors.

System 10 first instructs the operator to ascertain that the individual is in the supine position on a flat, non-tilted surface. System 10 then instructs the operator to place housing 12 under the neck of the individual and position it such that the marking on the top surface of housing 12 align with the neck/head of the individual. The recess of headrest 13 can also include pressure sensors to indicate correct neck positioning via an audible message or a light indicator.

Once the head of the individual is correctly placed (as determined by sensors in the recess of housing 12), face mask 22, which is designed for universal fit will then be ejected from housing 12 and system 10 will then instruct the operator to place face mask 22 over the nose and mouth of the individual. Once placed, face mask 22 will automatically switch on and oxygen will be provided to the individual. The flow rate of the oxygen will be between 10-15 liters per minute. The face mask reservoir will compensate the oxygen amount at patient inhale and enable a reduced oxygen flow rate and tank volume. An appropriate flow of oxygen will be supplied from tank 16 via a pre-determined regulator setting, if need be, such settings can be altered by the operator according to instructions provided by system 10 or a medical professional communicating therewith. Exchange of spent oxygen cylinders will be possible by a quick release connection system.

Face mask 22 can include a sensor for respiratory rate which can determine oxygen flow rate and/or oxygen pressure, thereby enabling system 10 to track respiration (See Example 1 for further detail). System 10 will issue a warning message if respiration decreases; a decrease due to incorrect head positioning will also be accompanied by a message indicating as such. In such cases, system 10 can then automatically operate mechanism 15 to modify the head angle while tracking respiratory parameters (inspiration/expiration ratio, respiration rate, respiration volume/min etc) via pressure and flow transducer positioned within face mask 22 until respiration is optimized. Alternatively, system 10 can issue instructions to the operator to modify the head angle (incrementally in a specific direction, flexion/extension) via mechanism 15 or tilting of housing 12 until a desired respiration parameters is achieved. Further description of sensors and data collected and analyzed and the face mask assembly is provided in Example 1 of the Examples section which follows.

During the above described process, the operator can communicate with emergency services and obtain further instructions if needed. If system 10 detects that the individual stops breathing, a warning message and instructions to start CPR will be issued by system 10. Specific instructions for locating the correct chest location for applying compression and instructions for applying the correct CPR rhythm and pressure will be issued by system 10.

During resuscitation, vital signs record unit 26 can record (to a storage device such as a memory chip) vital signs for real-time or delayed evaluation by a trained medical personnel. Vital signs can be measured using a wrist cuff 34 (FIG. 3) and the data can be transmitted (via wire or wirelessly) to the memory chip positioned inside housing 12.

Wrist cuff 34 can include a pulse oxymeter sensor which is positioned so as to contact the radial artery thereby providing oxymetry and pulse rate readings. Wrist cuff 34 can also include a PCO2 sensor, a blood pressure sensor and temperature sensor (wrist cuff 34 is further described in Example 1).

Alternatively, pulse rate and oxymetry can be measured via a finger tip sensor or a cutaneous sensor applied to the skin of the forehead or earlobe. System 10 can instruct the operator in as far as correct placement of the wrist cuff or skin-applied sensors and provide feedback if the sensors do not pick up any readings or if the wrist cuff is applied inappropriately. If a pulse is not detected, or if an irregular pulse is detected system 10 can also provide the operator with an alert indicating detections of abnormal readings and optionally also provide instructions as to how to perform chest compressions. Such alerts can also be relayed to the emergency medical services.

Although emergency situations in which the treated individual is unconscious or incapacitated require that system 10 be operated by a second individual, it will be appreciated that system 10 can also be self-operated by a conscious individual who is not feeling well.

In such cases, the individual simply follows the instructions provided by system 10 (as described above) and applies face mask 22 and wrist cuff 34. Since the individual is conscious and breathing unassisted, face mask 22 can be used while seated or not used at all. In any case, system 10 can collect vital signs from the individual and store the data or communicate it to a medical facility or a physician for further analysis. The data can be tracked for several minutes to hours in order to determine the medical condition of the individual. If need be, system 10 can be used to establish direct communication between the medical facility or physician and the individual in order to enable exchange of information. The tracked data can be used to decide if the individual is OK or needs to be transported to a medical facility. If system 10 detects that the condition of the individual is deteriorating, a medical responder can be alerted by system 10.

Thus, the present invention provides a resuscitation system which overcomes the limitations of prior art devices. The present system enables rapid and easy deployment in an easy to carry, single unit system which enables a layperson to perform basic resuscitation techniques without prior resuscitation experience. In its preferred configuration, the present system is designed as a single pack which is anatomically configured and optionally manually or automatically configurable to function as an airway-opening neck rest, oxygen supply, while also being configured for housing and protecting the functional components of the system from damage during storage and transport.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Respiratory Functions

The portable respiratory assist system of the present invention can incorporate sensors, transducers and software for identifying and correcting respiratory distress and failure.

As is described hereinabove, a first step in treating a subject involves placement of an oxygen face mask over the nose and mouth of the individual and placement of a wrist scuff cuff around the radial artery. Once placed, the system automatically switches on oxygen flow to deliver between 10-15 liters per minute of oxygen as well as monitor breathing and airway secretions and the wrist cuff communicates blood pressure, pulse and oxymetry data to the processing unit which is provided with a dedicated software application for processing sensor data.

A transducer positioned in the face mask provides the present system with outflow and inflow readings as well. Such reading can be converted into inspiration and expiration data as well as volume and breathing rate data by the processing unit running the dedicated software application to provide an indication (communicated via speaker or display) of the respiratory function of the subject as well as the physiological state thereof (preferably by integrating the face mask data with the data provided by the wrist cuff).

Figure 4:
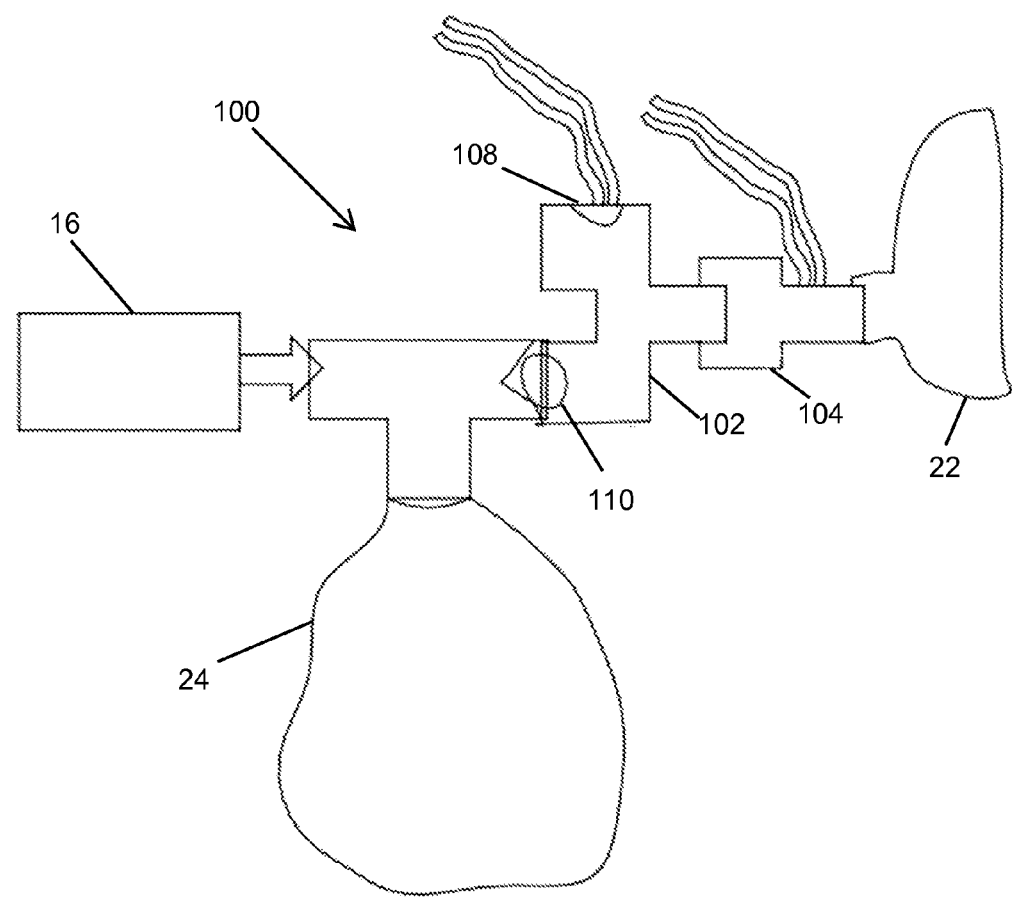
FIG. 4 schematically illustrates the face mask assembly used by the present system.

FIG. 4 illustrates the face mask assembly of the present system which is referred to herein as face mask assembly 100. Face mask assembly 100 includes a Y connector 102 and an in-line transducer 104 which is capable of measuring both inspired and expired gas flow intermittently. The transducer can be any pressure/flow transducer. Examples of suitable transducers include the D-Lite transducer by GE (www.ge-healthcare.com/euen/patient_monitoring/docs/Spirometry_M1 115724eng.pdf), the Hamilton transducer (www.envitec.com/download/media/00030876.pdf/e_mail_version_SpiroQuant_H.pdf) and the Versamed transducer www.wipo.int/pctdb/en/wads.jsp?IA=IL2002000613&LANGUAGE=EN&ID=id00 000000157201&VOL=33&DOC=00143f&WO=04/008961&WEEK=05/2004&TYPE=A1&DOC_TYPE=PAMPH&TOK=M7mMxJMfxfzPSQ3Lc2T92n6D2XY&PAGE=1

Face mask assembly 100 enables the patient to inhale large volumes of air through face mask 22 and reservoir valve 110, at a high frequency, exhausting the O2 volume in reservoir 24 and also enables atmospheric air to enter the face mask via atmospheric valve 108. The resistance of atmospheric valve 108 to air flow is higher than that of reservoir valve 110, and as such more 02 enriched gas is inhaled by the patient with each breath.

The present system can identify a leak between face mask 22 and the patient's face, by referring to a look up table describing the ratio between volumetric flows and patient pressure (mask pressure). Moreover, the identification of specific unsymmetrical flow patterns between inspiratory and expiratory stages can help calculate an average "hole size" for leak compensation or issue of alert.

Identification of Respiratory Distress

When a subject is suffering from airway blockage but is still capable of autonomous breathing, the inspiration waveform appears jagged with 5-20% deviations from the normal smooth waveform. Such an irregular inspiration waveform can point at secretions lodged in the airways, mechanical damage to the airway or incorrect head angle positioning.

Figure 5:
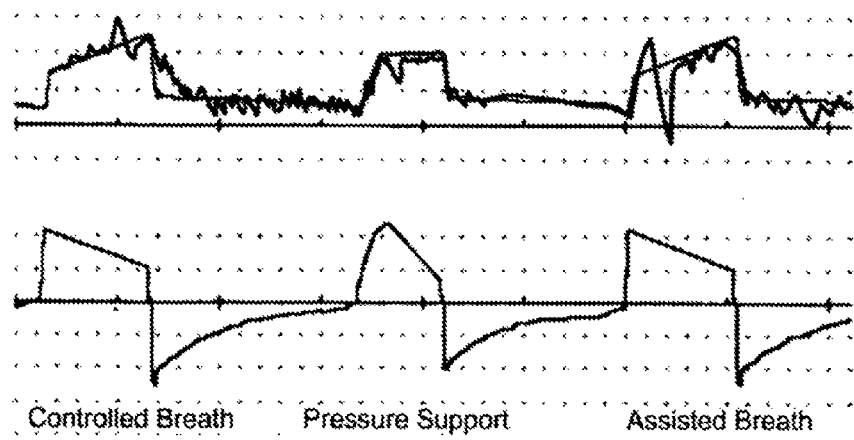
FIG. 5 illustrates a breathing waveform for a subject under controlled breath, pressure supported breath and assisted breath. The top waveform illustrates obstructed breathing under such scenarios.

The face mask of the present system can sense secretions and provide an operator of the present system with instructions to clear any such secretions from the airway or face mask. Secretions can be identified by using a sensitive flow transducer, that identifies distinctive flow patterns resulting from presence of secretions. For example, a signal with interrupted and spiky flow pattern during inspiration (FIG. 5) can be indicative of secretions.

If sensor data indicates that obstruction is likely due to head angle position, the present system can either instruct the operator to change the head angle, via direct flexion or extension of the head or via a manually operated mechanism Alternatively, the system can automatically operate such a mechanism which can include a motor or servo, or air bags positioned in the headrest until a desired angle is achieved as indicated by a change in breathing (measured by the transducer). The headrest can include accelerometers and/or gyros to track changes in head angles. In any case, any change in head angle is then followed by a period of monitoring and head angle repositioning if necessary until satisfactory breathing is established.

Data retrieved from the sensors can also be used to assess physiological parameters of the subject. The inspiratory/expiratory ratio calculated by the dedicated software can provide an indication as to the physiological condition of the subject. An optimal inspiratory/expiratory ratio is 1:2.5, a ratio greater than 1:3 can indicate impaired lung function caused by a stroke, trauma or other medical conditions. In addition, a respiration rate (in an adult subject) greater than 20/minute can also indicate general condition deterioration.

The present system can monitor inspiratory/expiratory ratio and respiration rate and provide the operator with a warning as well as automatically send a warning to a medical response team/hospital. In cases where an inspiratory/expiratory ratio persists for more than a predetermined time period, the present system can instruct the operator to change the flow rate and head angle or automatically change such parameters and monitor the subject for a change in condition.

As is mentioned above, the software of the present system can integrate the transducer and sensor data with heart monitoring, oxymetry and blood pressure data (which can be provided from the wrist cuff of the present system) to better qualify the state of the individual and to verify that the breathing data aligns with the wrist cuff data.

The wrist cuff can be an inflatable or elastic cuff positioned around the radial artery while applying slight pressure thereto. For blood pressure monitoring, the cuff can include an inflation/deflation mechanism for applying up to 180 mm Hg pressure to the radial artery. The wrist cuff can also include a transducer for measuring pulse rate, and pulse and oxymetry sensors as well as a temperature sensor. The wrist cuff can communicate sensor information (blood pressure, pulse, O2 saturation and temperature) to the processing unit of the present system via wired or wireless (e.g. RF) communication modes. Such information can then be integrated with the face mask sensors data and stored for later use by medical personal. In cases where a discrepancy between the face mask and wrist cuff data is detected, the system can provide the operator with a warning and instructions to reposition the face mask and/or wrist cuff.

The transducer can also be used to measure the inspiratory and expiratory volumes. A healthy adult breaths at a rate of 12-15 breaths/minute with each breath being ~500 cc in volume. Thus an average individual breaths about 7.5 liters/minute. If the present system identifies a drop in breathing capacity below 3 L/min, or a rise to above 13 L/min, it provides a warning to the operator and indicates a possible emergency situation (communicated via speaker or display) caused by stroke, trauma weakness or incorrect face mask/wrist cuff positioning. In any case, appropriate instruction would then be provided to the operator and alerts sent to medical response team/hospital.

The system can then automatically modify the head angle of the subject or instruct the operator to do so until satisfactory volume readings are obtained. The system can also modify the oxygen saturation and flow rate.

It will be appreciated that the present system can also be used in situations where an individual is not feeling well but is capable of operating the system without assistance. In such situations, the individual can self position the face mask and wrist cuff in a seated or lying position. The system can then provide the individual with O2 enriched air and monitor vital signs as well as breathing. The sensor data can then be used to provide the individual with instructions (to modify treatment) and/or contact a medical response team or treating physician for further instructions (e.g. continue treatment, go to a hospital or wait for a medical response team).

Example 2

Medical Emergency Scenario

An individual loses consciousness and is assisted by a second individual to a supine position. The headrest of system 10 is positioned under the neck of the individual and the system is activated. The system then performs the following:
1. The system in accordance with the algorithm verifies the sensor data by examining and comparing the wrist cuff and face mask data to identify whether breathing is prevented by incorrect head angle etc. If need be and according to sensor data, the head angle of the subject is modified as described above.
2. No pulse detection-system immediately alerts the medical center. The medical center will receive the medical data and be able to analyze and assess the patient's condition.
3. The medical center will be able to expedite arrival of medical staff.
4. The system will prompt the operator how to perform CPR (using audio and visual messages) until the arrival of medical staff. CPR instructions include location of the operator's hands, timing and rhythm instructions.
5. Oxygen is continuously provided to the patient through the face mask. The system will indicate if the patient starts breathing again on his own and send the data to the medical center.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention

What is claimed is:

1. A system comprising:
    a ventilation device; and
    a vital signs tracking device;
    an airway opening device; and
    a housing enclosing the ventilation device, the housing shaped as a neck support and further including on its upper surface a head rest designed for accepting the neck of a subject and supporting it in an extended position;
    wherein the system is configured to facilitate an opening of an airway of the subject in a supine position using the airway opening device, by alerting or instructing a user upon an attempt to open an airway
    wherein the alerting or instructing is based on real time measurements of the vital signs of the subject tracked by the vital signs tracking device during the attempt to open an airway; and
    wherein the housing comprises a mechanism to change at least one of the shape of the headrest, the height of the headrest, the position of the housing, and the angle of the housing, for modifying a head angle of the subject when in said supine position.

2. The system according to claim 1, wherein the ventilation device is further configured, upon a successful opening of an airway, to supply oxygen to the subject such that oxygen supply is sufficient, based on real time measurements of the vital signs of the subject tracked during oxygen supply.

3. The system according to claim 1 further configured, upon a successful opening of an airway, to supply oxygen to the subject and to alert the user whenever the oxygen supply is non-satisfactory, based on real time measurements of the vital signs of the subject tracked during oxygen supply.

4. The system according to claim 1, further comprising a communications unit configured to: (i) transmit data collected via said vital signs tracking device to a remote location and (ii) receive data and/or instructions from the remote location.

5. The system according to claim 4, wherein the transmission of collected data from the system, and the receipt of the data and/or instructions from the remote location are carried out automatically.

6. The system according to claim 1, wherein the system is further configured to record over time the tracked vital signs of the subject and treatment carried out by the user, for later analysis.

7. The system according to claim 1, further comprising a location tracking unit for determining a geographic location of the system.

8. The system according claim 1, wherein said mechanism is operated manually by the user in accordance with instructions presented by the system which are further based on the tracked vital signs.

9. The system according to claim 1, wherein said mechanism is operated automatically based on the tracked vital signs.

10. The system according to claim 1, wherein said mechanism includes a motor, a servo or an inflatable bladder.

11. The system according to claim 1, wherein said ventilation device includes a pressurized oxygen source and a face mask.

12. The system according to claim 11, wherein said ventilation device includes a respiration sensor.

13. The system according to claim 12, wherein said respiration sensor is positioned in a reservoir of said face mask.

14. The system according to claim 12, wherein data from said respiration sensor is useable for determining a respiration parameter that is at least on of: inspiration/expiration ratio, respiration rate, and respiratory volume.

15. The system according to claim 1, wherein the vital signs tracking device is configured to track at least one of: a respiration rate, a heart rate, blood pressure, pulse rate, and blood oxygenation.

16. The system according to claim 1, wherein the housing includes a recess at a top surface thereof, said recess being designed for accommodating a neck of said subject in a manner which extends said neck to open an airway of said subject.

17. The system according to claim 1, wherein said vital signs tracking device is configured as a wrist cuff.

* * * * *